United States Patent [19]

Mead et al.

[11] 4,025,583

[45] May 24, 1977

[54] AMINE ADDUCTS OF ETHYL OLEYL ACID ORTHOPHOSPHATE

[75] Inventors: Theodore C. Mead, Port Arthur; Richard T. McDill, Houston; Ralph P. Chesluk; Norman R. Odell, both of Nederland, all of Tex.

[73] Assignee: Texaco Inc., New York, N.Y.

[22] Filed: Jan. 12, 1976

[21] Appl. No.: 648,595

Related U.S. Application Data

[62] Division of Ser. No. 455,447, March 27, 1975, Pat. No. 3,979,308.

[52] U.S. Cl. ............................ 260/925; 260/293.65; 260/347.7
[51] Int. Cl.² ............................................. C07F 9/09
[58] Field of Search ............................. 260/925

[56] References Cited

UNITED STATES PATENTS 2,387,537  10/1945  Smith et al. .................. 260/925
2,408,232  9/1946  Smith et al. .................. 260/925
2,863,904  12/1958  Cantrell et al. ............... 260/925
3,460,923  8/1969  Dorer, Jr. .................. 260/925UX

*Primary Examiner*—Anton H. Sutto
*Attorney, Agent, or Firm*—Carl G. Ries; Thomas H. Whaley; Kenneth R. Priem

[57] ABSTRACT

Disclosed are lubricant compositions containing adducts of an amine with a phosphate ester of the formula:

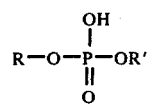

wherein R is hydrogen or alkyl having up to 25 carbon atoms in the chain, R' is hydrogen or alkyl having up to 7 carbon atoms except only one of R and R' can be hydrogen or octyl.

2 Claims, No Drawings

AMINE ADDUCTS OF ETHYL OLEYL ACID ORTHOPHOSPHATE

This is a division, of application Ser. No. 455,447, filed Mar. 27, 1975, now U.S. Pat. No. 3,979,308.

This invention relates to the preparation of novel and useful lubricating compositions. More particularly, the invention concerns lubricating oil compositions comprising a base mineral oil and a specified adduct of an amine with a phosphate ester whereby the viscosity index of the oil is substantially improved.

In the prior art, U.S. Pat. No. 2,983,678/9 disclosed the use of rare earth salts of ethyl oleyl acid as viscosity index (VI) improvers. Undesirably, formulations containing these additives proved deficient in storage stability, reporducibility of viscosities and compatibility with conventional lubricating oil additives. Additionally, these salts, being partly inorganic, are not suitable for use is ashless or low metal fomulations.

In accordance with the invention, there are provided improved lubricating compositions comprising a major proportion of an oil of lubricating viscosity and from 0.01 to 10 percent by weight thereof of at least one adduct of an amine with a phosphate ester of the formula:

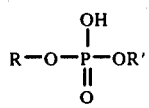

wherein R is hydrogen, alkyl having up to 25 carbon atoms and R' is hydrogen or alkyl having up to 7 carbons, except that only one of R or R' can be hydrogen or octyl.

The phosphate ester should be present preferably in 0.1 to 1.0 weight percent of base oil and may be used in proportions of 0.01 to 10.0 weight percent. The amine should be present in an amount stoichiometrically equivalent to phosphate ester and preferably in a proportion such that three moles of amine are present per mole of phosphate. The operable range includes 1.0 to 10.0 moles of amine per mole of phosphate ester.

Both naphthenic and paraffinic distillates can be treated by the method of the invention; for best results, these should be 20 weight or lighter, since relatively larger amounts of adduct are needed in heavy oils. Naphthenic and paraffinic residual stocks, undistilled crudes, extracts from solvent refining also respond to the method of the invention. Oils which have already been subjected to deasphalting, dewaxing, solvent refining, clay contacting, acid treating, hydrogenation, or any combination of the foregoing processes are amenable to the method of the invention.

The adduct may be prepared in concentrated form in any convenient base oil or the amine and phosphate ester may be added to the bulk of the oil to be treated separately. The former method is preferred. If the former method is used, the amine-ester concentrate is best heated to 225° F. before being added to the base oil. This assures complete solution of the amine and phosphate in the concentrate.

The amine is of the general formula:

wherein the substituents can be either hydrogen, alkyl or aryl groups having up to 30 carbons atoms. As shown by the data of Table V, below, the nature of the amine is not critical. Thus typical amines include methyl benzyl amine, isobutylamine N-cyclohexylpiperidine and furfuryl amine. Only adducts of ethyl oleyl acid orthophosphate have been found to give reproducible blend viscosities.

The unobvious and unexpected results obtained with the invention are disclosed hereinbelow.

In Table I below there are shown the effects of amine-phosphate ester adducts on the viscosity and viscosity index of some represenative base oils: a 300 second naphthene distillate a 5 weight solvent neutral oil, a 20 weight solvent neutral oil and a dewaxed (but unrefined) 20 weight wax Distillate.

In all cases, a liquid concentrate of amine and phosphate ester was prepared and added volumetrically to the base oil in question.

Ethyl oleyl acid orthophosphate (3.1 grams) and methyl benzyl amine (3 ml) were combined in 100 ml of 55 Pale Oil* and heated with stirring to 225° F. Ten or twenty milliliter portions of the cooled concentrate were added to the base oil, and the resultant blend stirred at room temperature for a few minutes.

* 55 Pale Oil is here and hereafter used to designate a 55 SUS viscosity at 100° F. naphthene pale oil.

The slight decrease in 100° F. viscosity, which will be noted for the resultant blends, is entirely attributable to the light carrier oil used to prepared the concentrate.

In Table II, below there are summarized the effect of ethyl oleyl acid orthophosphate alone, methyl benzyl amine alone, and the amine-phosphate combination on the viscosities and viscosity indices of 300 SUS at 100° F viscosity naphthene distillate. All were added in light carrier oil; this light oil comprises five percent of the resultant blend.

The explanatory data of Table III, shows that other amines of various structural types may be effectively used with ethyl oleyl acid orthophosphate as a viscosity index improver.

A major objection to the use of rare earth salts of dialkyl acid orthophosphates was the widely varying viscosities and viscosity indices obtained from presumably identical blends of salts and base oil. To demonstrate the superiority of the amine-phosphate adduct in this respect, four blends of unrefined, dewaxed 20 weight wax distillate were treated with sufficient ethyl oleyl acid orthophosphate methyl benzyl amine adduct to bring about a viscosity index because of about 50 percent. Two samples were taken from each blend and the viscosities of each of the eight samples determined; these are listed in Table IV. Satisfactory agreement is observed between samples from the same blends and among various blends.

TABLE I

EFFECT OF ETHYL OLEYL ACID ORTHOPHOSPHATE-ORGANIC AMINE COMPLEXES ON VARIOUS OILS

| Base Oil | Quantity (ml) | Ethyl Oleyl Acid Orthophosphate (g) | Methyl Benzyl Amine (ml) | Carrier Oil | Quantity of Carrier (ml) | Kinematic Viscosity, cs 100° | 210° | VI |
|---|---|---|---|---|---|---|---|---|
| 300 Pale Stock | — | — | — | — | — | 66.44 | 6.46 | 20 |
| 300 Pale Stock | 200 | 0.31 | 0.3 | 55 Pale | 10 | 60.73 | 7.34 | 88* |
| Solvent Neutral-5 | — | — | — | — | — | 20.42 | 3.92 | 91 |
| Solvent Neutral-5 | 200 | 0.31 | 0.3 | 55 Pale | 10 | 19.70 | 5.19 | 231* |
| Solvent Neutral-20 | — | — | — | — | — | 73.06 | 8.27 | 88 |
| Solvent Neutral-20 | 200 | 0.62 | 0.6 | 55 Pale | 20 | 57.92 | 10.13 | 176** |
| Dewaxed WD-20 | — | — | — | — | — | 177.04 | 12.24 | 49 |
| Dewaxed WD-20 | 200 | — | 0.3 | 55 Pale | 10 | 148.16 | 11.06 | 51 |
| Dewaxed WD-20 | 200 | 0.31 | 0.6 | 55 Pale | 10 | 148.75 | 11.58 | 62* |
| Dewaxed WD-20 | 200 | 0.62 | | 55 Pale | 20 | 129.34 | 11.32 | 77* |

*Average 8 runs
**Average 6 runs

TABLE II

EFFECTS OF ETHYL OLEYL ACID ORTHOPHOSPHATE AND METHYL BENZYL AMINE ON 300 PALE STOCK

| Base Oil | Quantity (ml) | Phosphate (g) | Amine (ml) | Carrier | Quantity (ml) | Kinematic Visc. 100° F. | 210° F. | VI |
|---|---|---|---|---|---|---|---|---|
| 300 Pale Stock | — | — | — | — | — | 66.44 | 6.46 | 20 |
| 300 Pale Stock | 200 | — | — | 55 Pale Oil | 10 | 58.80 | 6.07 | 26 |
| 300 Pale Stock | 200 | 0.31 | — | 55 Pale Oil | 10 | 62.76 | 6.26 | 21* |
| 300 Pale Stock | 200 | — | 0.3 | 55 Pale Oil | 10 | 59.75 | 6.13 | 24** |
| 300 Pale Stock | 200 | 0.31 | 0.3 | 55 Pale Oil | 10 | 60.73 | 6.46 | 88*** |

*Average 7 Runs
**Average 6 Runs
***Average 8 Runs

TABLE III

EFFECTIVENESS OF ETHYL OLEYL ACID ORTHO PHOSPHATE WITH VARIOUS AMINES WITH RESPECT TO VI IMPROVEMENT OF 300 PALE STOCK

| Base Oil | Quantity (ml) | EOP* (g) | Amine | Quantity (ml) | Kinematic Viscosity, cs 100° | 210° | VI |
|---|---|---|---|---|---|---|---|
| 300 Pale Stock | — | — | — | — | 66.44 | 6.46 | 20 |
| 300 Pale Stock | 1000 | 3.1 | α-methylbenzyl amine | 3 | 68.99 | 9.97 | 138 |
| 300 Pale Stock | 1000 | 3.1 | N-cyclohexylpiperidine | 3 | 112.52 | 16.42 | 168 |
| 300 Pale Stock | 1000 | 3.1 | Isobutyl amine | 3 | 81.69 | 12.05 | 152 |
| 300 Pale Stock | 1000 | 3.1 | Furfuryl amine | 3 | 84.33 | 13.92 | 181 |

*Ethyl oleyl acid orthophosphate

TABLE IV

REPRODUCIBILITY OF VISCOSITY INDEX IMPROVEMENT

A. Concentrate containing 3.1 grams of ethyl oleyl acid orthophosphate and 3 ml methyl benzyl amine in 100 ml of 55 Pale Oil is prepared at 275° F. Ten milliliter portions of concentrate are added to each of four 200 ml portions of unrefined, dewaxed 20 weight wax distillate. Each sample submitted for duplicate determination of 100° F. and 210° F. kinematic viscosity:

| | Viscosity at 100° | 210° | VI |
|---|---|---|---|
| Base Oil | 177.04 | 12.24 | 49 |
| Blend 1 | 148.98 | 11.49 | 61 |
| | 148.73 | 11.60 | 62 |
| Blend 2 | 148.46 | 11.56 | 62 |
| | 150.04 | 11.67 | 63 |
| Blend 3 | 148.92 | 11.70 | 64 |
| | 148.22 | 11.55 | 61 |
| Blend 4 | 148.78 | 11.60 | 62 |
| | 148.90 | 11.49 | 60 |

B. Concentrate prepared in A is added in twenty milliliter portions to/200 ml portions of the same base oil. Two samples of each blend tested:

| Blend 1 | 128.98 | 11.25 | 76 |
|---|---|---|---|
| | 128.66 | 11.36 | 78 |
| Blend 2 | 129.47 | 11.37 | 78 |
| | 129.49 | 11.38 | 78 |
| Blend 3 | 129.53 | 11.29 | 76 |
| | 130.26 | 11.35 | 76 |
| Blend 4 | 129.05 | 11.30 | 76 |
| | 129.32 | 11.25 | 75 |

TABLE V

VI IMPROVEMENT OF 300 PALE STOCK: EFFECT OF AMINE STRUCTURE IN ETHYL OLEYL ACID ORTHOPHOSPHATE ADDUCTS

| Amine | Wt % | EOAP, Wt. % | Carrier | Vol. % | Kin. Vis, cs 100° F. | 210° F. | VI |
|---|---|---|---|---|---|---|---|
| None | — | — | — | — | 66.44 | 6.46 | 20 |
| Oleylamine ("Armeen-O") | 0.15 | 0.17 | — | — | 68.05 | 7.98 | 90 |

-continued

TABLE V : VI IMPROVEMENT OF 300 PALE STOCK: EFFECT OF AMINE STRUCTURE IN ETHYL OLEYL ACID ORTHOPHOSPHATE ADDUCTS

| Amine | Wt % | EOAP, Wt. % | Carrier | Vol. % | Kin. Vis, cs 100° F. | 210° F. | VI |
|---|---|---|---|---|---|---|---|
| α-Methylbenzylamine | 0.31 | 0.30 | — | — | 68.99 | 9.97 | 138 |
| N-cyclohexylpiperidine | 0.31 | 0.30 | — | — | 112.52 | 16.42 | 168 |
| Isobutylamine | 0.31 | 0.30 | — | — | 81.69 | 12.05 | 152 |
| Furfurylamine | 0.31 | 0.30 | — | — | 84.33 | 13.92 | 1 |
| None | — | — | 55 Pale Oil Filt. | 13 | 48.21 | 5.48 | 23 |

To show shear stability and storage stability solvent neutral oil 5 blend containing the EOAP -α- methyl-benzyl-amine adduct was studied. It underwent no decrease in 100° F viscosity under the conditions of the 20-pass Fuel Injector Shear Stability Test. Some increase in 210° F. viscosity did result; viscosity index across the test underwent a nominal increase, although both sheared and unsheared blends were too high to calculate in the normal manner. These data are summarized in Table VI.

The SNO-5, EOAP, MBA blend listed in Table V was tested at the end of six and 171 days standing at room temperature. Some descrease in 210° F. viscosity occurred after the longer period. Viscosity index remained above 250 in all cases. Data are included in Table VI.

TABLE VI

SHEAR AND STORAGE STABILITY OF SNO-5 CONTAINING ETHYL OLEYL ACID ORTHIOPHOSPHATE-α-METHYLBENZYLAMINE ADDUCT

| | Kinematic 100° F., cs | Viscosity 210° F., cs | VI | Percentage Decrease in 100° F. Viscosity |
|---|---|---|---|---|
| 1. SNO-5 | 20.42 | 3.92 | 91 | |
| 2. SNO-5 plus 5.0 vol% 55 Pale Oil | 19.54 | 3.80 | 88 | |
| 3. SNO-5 plus EOAP (0.155 wt%), α-methylbenzylamine (0.16 wt%), 5.0 vol% 55 Pale Oil | 20.01 | 7.32 | 250 | |
| 4. Above, after 20-pass FISST (sample 1) | 20.36 | 8.07 | 300 | |
| 5. Above, after 20-pass FISST (sample 2) | 20.35 | 8.80 | 300 | |
| 6 No. 3, After six days at room temperature | 20.23 | 6.82 | 300 | 0 |
| 7. NO. 3, After 171 days at room temperature | 20.11 | 6.77 | 300 | 0 |

Table VII, below, shows the VI enhancing effect of other adducts according to the invention. As pointed out previously, however, only adducts of ethyl oleyl acid orthophosphate give reproducible blend viscosities. The other adducts, in common therewith, have utility as pour point modifiers, oil thickening agents and as oil spill coagulates.

TABLE VII

VI-ENHANCING EFFECT: VARIOUS AMINE PHOSPHATE ADDUCTS

| Acid Phosphate | Wt. % | Amine | Vol. % | | Kinematic Viscosity, cs 100° F | 210° F | VI |
|---|---|---|---|---|---|---|---|
| In 300 Pale Stock | | | | | | | |
| 300 Pale Stock | | | | | 66.44 | 6.46 | 20 |
| 300 Pale Stock containing 4.8 vol. % 55 Pale Oil (used in asterisked cases below) | | | | | 58.80 | 6.07 | 26 |
| *amyl | 0.15 | hexyl | 0.15 | | 59.46 | 6.09 | 23 |
| amyl | 0.31 | oleyl | 0.30 | | 68.47 | 6.62 | 24 |
| butyl | 0.15 | isobutyl | 0.15 | | 68.20 | 6.60 | 24 |
| *butyl | 0.15 | hexyl | 0.15 | | 59.66 | 6.14 | 25 |
| butyl | 0.31 | oleyl | 0.30 | | 68.06 | 6.63 | 26 |
| *isooctyl | 0.15 | isobutyl | 0.15 | | 60.55 | 6.19 | 25 |
| *isooctyl | 0.15 | α-methylbenzyl | 0.15 | | 60.49 | 6.16 | 23 |
| isooctyl | 0.31 | oleyl | 0.30 | | 68.02 | 6.64 | 27 |
| oleyl | 0.31 | isobutyl | 0.30 | | 68.22 | 6.64 | 26 |
| *oleyl | 0.15 | hexyl | 0.15 | | 59.98 | 6.10 | 21 |
| phenyl | 0.15 | isobutyl | 0.15 | | 67.82 | 6.49 | 18 |
| phenyl | 0.31 | oleyl | 0.30 | | 68.68 | 6.59 | 24 |
| stearyl | 0.31 | isobutyl | 0.30 | | 68.74 | 6.54 | 18 |
| stearyl | 0.31 | N-cyclohexylpiperidine | 0.30 | | 75.82 | 6.50 | < 0 |
| | | | | ck | 75.54 | 10.83 | 43 |
| | | | | ck | 74.03 | 6.71 | 11 |
| stearyl | 0.30 | ethylhexyl | 0.30 | | 67.91 | 6.58 | 23 |
| stearyl | 0.31 | N,N-dimethylbenzyl | 0.30 | | 68.99 | 7.40 | 67 |
| | | | | ck | 68.27 | 7.32 | 66 |
| | | | | ck | 68.04 | 6.54 | 20 |
| | | | | ck | 67.54 | 6.51 | 22 |
| | | | | ck | 68.01 | 6.57 | 22 |
| stearyl | 0.30 | dipropyl | 0.30 | | 79.11 | 6.77 | < 0 |
| stearyl | 0.30 | furfuryl | 0.30 | | 68.18 | 6.72 | 32 |
| stearyl | 0.15 | hexyl | 0.15 | | 60.02 | 6.14 | 20 |
| *stearyl | 0.30 | N-methylaniline | 0.30 | | 67.52 | 6.56 | 23 |
| stearyl | 0.30 | methylcyclohexyl | 0.30 | | 67.64 | 10.71 | 159 |
| stearyl | | | | ck | 67.60 | 5.22 | < 0 |
| | | | | ck | 68.27 | 7.36 | 67 |

TABLE VII-continued

VI-ENHANCING EFFECT: VARIOUS AMINE PHOSPHATE ADDUCTS

| Acid Phosphate | Wt. % | Amine | Vol. % | | Kinematic Viscosity, cs 100° F | 210° F | VI |
|---|---|---|---|---|---|---|---|
| | | | | ck | 73.33 | 6.00 | < 0 |
| Stearyl | 0.30 | oleyl | 0.30 | | 68.70 | 6.56 | 19 |
| Stearyl | 0.30 | 2-picoline | 0.30 | | 69.96 | 10.84 | 156 |
| | | | | ck | 69.69 | 6.88 | 38 |
| | | | | ck | 71.16 | 6.62 | 14 |
| Stearyl | 0.30 | 3-picoline | 0.30 | | 70.36 | 6.49 | 8 |
| Stearyl | 0.30 | 4-picoline | 0.30 | 70.54 | 6.58 | 14 | |
| In "SNO"-10 (81.0% SNO-5 14.3% SNO-20, 4.8% 55 Pale Oil Filtered) | | | | | | | |
| SNO-10 | | | | | 28.51 | 4.87 | 102 |
| *amyl | 0.16 | α-methylbenzyl | 0.15 | | 27.99 | 4.76 | 100 |
| *butyl | 0.16 | α-methylbenzyl | 0.15 | | 28.10 | 4.82 | 101 |
| *oleyl | 0.16 | α-methylbenzyl | 0.15 | | 28.20 | 4.81 | 100 |
| *phenyl | 0.16 | α-methylbenzyl | 0.15 | | 28.43 | 4.79 | 94 |
| *stearyl | 0.16 | α-methylbenzyl | 0.15 | | 28.29 | 4.79 | 97 |
| In Dewaxed WD-20 containing 4.8% 55 Pale Oil Filtered | | | | | | | |
| DW-WD-20 | | | | | 143.48 | 10.92 | 53 |
| isooctyl | 0.16 | isobutyl | 0.15 | | 150.90 | 11.18 | 51 |
| isooctyl | 0.16 | α-methylbenzyl | 0.15 | | 148.78 | 11.10 | 51 |

Adduct formed in 55 Pale Oil Filtered concentrate containing 3 weight percent phosphate and heated to 225° F.
N. B. Where check viscosity analyses are not indicated, satisfactory check values were obtained.

The adducts of the invention are compatible with conventional lubricating oil additives including antioxidants corrosion inhibitors, foam suppressants and the like. Being entirely organic the adducts are suitable in ashless or low metal formulations. They are effective to improve viscosity index at extremely low dosages. Thus, a base stock showed a VI improvement of 55 to 79 with only 590 parts per million of the adducts.

The oil component of this composition can be any mineral oil compatible with carrying out lubricating functions in the various locations where metal contact occurs in the art. The viscosity ranges of the oil of the above composition may vary widely.

The specific viscosity would naturally depend upon the service for which the composition is designed.

The level of these various components in the oil will depend upon the resultant properties desired.

What is claimed is:

1. A composition of matter comprising ethyl oleyl acid orthophosphate and the adduct of an amine of the formula:

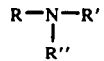

wherein the substituents are either hydrogen, alkyl or aryl groups having up to 30 carbon atoms.

2. A composition of matter comprising the adduct of an amine and ethyl oleyl acid orthophosphate.

* * * * *